United States Patent [19]

Norcini et al.

[11] Patent Number: 5,739,123

[45] Date of Patent: Apr. 14, 1998

[54] PHOSPHINIC ACID DERIVATIVES WITH METALLOPEPTIDASE INHIBITORY ACTIVITY

[75] Inventors: Gabriele Norcini, Vizzola Ticino; Daniela Botta, Como; Francesco Santangelo, Milan; Gabriele Morazzoni, Lainate, all of Italy

[73] Assignee: Zambon Group S.p.A., Vicenza, Italy

[21] Appl. No.: 750,035

[22] PCT Filed: Jun. 16, 1995

[86] PCT No.: PCT/EP95/02343

§ 371 Date: Nov. 27, 1996

§ 102(e) Date: Nov. 27, 1996

[87] PCT Pub. No.: WO95/35302

PCT Pub. Date: Dec. 28, 1995

[30] Foreign Application Priority Data

Jun. 21, 1994 [IT] Italy .................... MI94A1291

[51] Int. Cl.[6] .................................................. A61K 31/66
[52] U.S. Cl. ................... 514/119; 558/181; 560/38; 560/190; 560/211; 562/8; 562/15
[58] Field of Search ........................ 514/119; 562/15

[56] References Cited

U.S. PATENT DOCUMENTS

| | | | |
|---|---|---|---|
| 4,379,146 | 4/1983 | Greenlee et al. | 424/177 |
| 4,396,772 | 8/1983 | Petrillo | 548/414 |
| 4,432,972 | 2/1984 | Karanewsky et al. | 424/177 |
| 4,814,484 | 3/1989 | Wissmann | 560/39 |
| 5,151,414 | 9/1992 | Casagrande et al. | 514/114 |
| 5,155,100 | 10/1992 | Erion | 514/119 |
| 5,250,522 | 10/1993 | Lombaert | 514/114 |
| 5,451,608 | 9/1995 | Santangelo et al. | 514/674 |

FOREIGN PATENT DOCUMENTS 2109793  6/1993  United Kingdom .
9314112  7/1993  WIPO .

OTHER PUBLICATIONS

Merz et al., "Free Energy Perturbation Simulations of the Inhibition of Thermolysin: Prediction of the Free Energy of Binding of a New Inhibitor", *J. Am. Chem. Soc.*, vol. 111, No. 15 (1989), pp. 5649–5658.

Mookhtiar, K.A. et al., "Phosphonamidate Inhibitors of Human Neutrophil Collagenase". *Biochemistry*, vol. 26, No. 7 (1987), pp. 1962–1965.

McMahon et al., "Phosphoramidon Blocks the Pressor Activity of Porcine Big Endothelin-1-(1-39) In Vivo and Conversion of Big Endothelin-1-(1-39), 2 Endothelin-1-(1-21) In Vitro", *Proceedings National Academy of Science*, vol. 88 (Feb. 1991), pp. 703–707.

(List continued on next page.)

*Primary Examiner*—Michael L. Shippen
*Attorney, Agent, or Firm*—Watson Cole Stevens Davis, P.L.L.C.

[57] ABSTRACT

Compounds of formula (I),

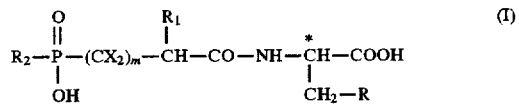

wherein R is a biphenyl group optionally substituted, by one or more substituents, the same or different selected among halogen atoms, hydroxy groups, alkoxy, alkyl thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, momo- or di-alkylamino groups having from 1 to 6 carbon atoms in the alkyl moiety, mono- or di-alkylaminocarbonyl groups having from 1 to 6 carbon atoms in the alkyl moiety; $R_1$ is a hydrogen atom, a straight or branched $C_1$–$C_6$ alkyl group or an arylalkyl group having from 1 to 6 carbon atoms in the alkyl moiety wherein the aryl is a phenyl, a biphenyl, a napthyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety; $R_2$ is a straight or branched $C_1$–$C_6$ alkyl group, optionally containing one or more fluorine atoms or one or more —NH— groups, an arylalkyl, an arylcarbonylaminoalkyl, an arylalkylcarbonylaminoalkyl or an arylaminocarbonylalkyl group having from 1 to 6 carbon atoms and optionally one or more —NH— groups in the alkyl moiety, the aryl being optionally substituted by one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono-or di-alkylamino groups having from 1 to 6 carbon atoms in the alkyl moiety, mono- or di-alkylaminocarbonyl groups having from 1 to 6 carbon atoms in the alkyl moiety; m is 0 or 1; X is a hydrogen or fluorine atom; the carbon atom marked with an asterisk is an asymmetric carbon atom; and their pharmaceutically acceptable salts, are described. The compounds of formula (I) are endowed with a mixed ACE-inhibitory and NEP-inhibitory activity and are useful in the treatment of cardiovascular diseases.

8 Claims, No Drawings

OTHER PUBLICATIONS

Fukuroda, T. et al., "Inhibition of Biological Action of Big Endothelin-1 by Phosphoramidon", *Biochemical and Biophysical Research Communication*, vol. 172, No. 2 (Oct. 30, 1990), pp. 390–395.

Rich, H. David, *"Peptidase Inhibitors" in Comprehensive Medicinal Chemistry : The Rational Design, Mechanistic Study & Therapeutic Application of Chemical Compounds*, vol. 2 (Pergamon Press PLC), pp. 391, 394, 395, 403, 410, 434–441 (1990).

Kam, C.M. et al., "Inhibition of Thermolysin and Carboxy Peptidase A Biphosphoramides", *Biochemistry*, vol. 18, No. 14 (1979), pp. 3032–3038.

Morgan, et al. Differential Binding Energy: A detailed Evaluation of the Influence of Hydrogen Bonding and Hydrophobic Groups on the Inhibition of Thermolysin by Phosphorus–Containing Inhibitors, J. Amer. Chem. Society (1991) 113, pp. 297–307.

Bertenshaw et al Phosphorus Inhibitors of Endothelin Converting Enzyme: Effects of teh Electronic Nature of phosphorus on Inhibitory Potency. J. Med. Chem 1993, vol. 36, No. 1 pp. 173–176.

De Lambert et al. Dual Inhibition of Neutral Endopeptidase and Angiotensin–converting enzyme by N–Phosphonnomethyl and N–Carboxyalkyl Dipeptides, Bioorg. Med. Chem. Lett. (BMCLE8.0960894X) 94; vol. 4 (22) pp. 2715–2720 (1994).

European Search Report (1995).

PHOSPHINIC ACID DERIVATIVES WITH METALLOPEPTIDASE INHIBITORY ACTIVITY

The present invention relates to phosphinic acid derivatives and, more particularly, it relates to phosphinic acid derivatives useful in the treatment of cardiovascular diseases as metallopeptidase inhibitors.

The pharmacologic interest towards the study of metallopeptidase inhibitory molecules derives from the role that said enzymes exert on the level of the cardiocirculatory system.

It is well-known, in fact, that compounds with angiotensin converting enzyme (ACE) inhibitory activity are mainly useful in the treatment of hypertension and of heart failure in that they inhibit the formation of angiotensin II, a substance which increases the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase enzyme (NEP), also called enkephalinase, are useful as vasodilators in that the NEP enzyme is responsible for the inactivation, not only of endogenous enkephaline, but also of atrial natriuretic factor (ANF), a vasodilator hormone secreted by heart.

Therefore, even exerting their action on the cardiovascular system with different mechanisms of action, the compounds with metallopeptidase inhibitory activity are generally used, alone or in combination, in the treatment of hypertension, renal failure and congestive heart failure.

In the U.S. Pat. No. 4,396,772 (Squibb & Sons, Inc.) some phosphinic acid derivatives and, more particularly, some phosphinyl alkanoyl amino acids are described as ACE-inhibitors.

As described by Brandley P. Morgan et al. in Journal of the American Chemical Society, 1991, 113, 297–307, some phosphinic acid derivatives and, particularly, the compound of formula

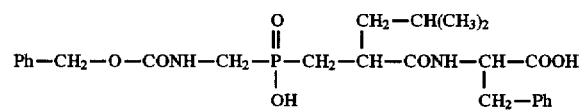

wherein Ph is a phenyl group, resulted to be endowed with inhibitory activity towards thermolysin, an endopeptidase of bacterial origin. Successively, as described by Stephen R. Bertenshaw et al. in Journal of Medicinal Chemistry, 1993, 36, 173–176, some phosphinic acid derivatives having a dipeptide moiety analogous to that of phosphoramidon, a well-known molecule with ECE-inhibitory activity, resulted to be devoid of any significant ECE-inhibitory activity. Now we have found phosphinic acid derivatives which are endowed with angiotensin converting enzyme as well as neutral endopeptidase enzyme inhibitory activity (mixed ACE/NEP inhibitory activity) which renders them particularly useful in the cardiovascular therapy. Therefore, object of the present invention are the compounds of formula

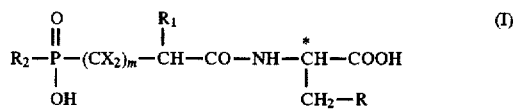

wherein

R is a biphenyl group optionally substituted by one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_1$ is a hydrogen atom, a straight or branched $C_1$–$C_6$ alkyl group or an arylalkyl group having from 1 to 6 carbon atoms in the alkyl moiety wherein the aryl is a phenyl, a biphenyl, a naphthyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_2$ is a straight or branched $C_1$–$C_6$ alkyl group, optionally containing one or more fluorine atoms or optionally one or more —NH— groups, an arylalkyl, an arylcarbonylaminoalkyl, an arylalkylcarbonylaminoalkyl or an arylaminocarbonylalkyl group having from 1 to 6 carbon atoms and optionally one or more —NH— groups in the alkyl moiety, the aryl being optionally substituted by one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

m is 0 or 1;

X is a hydrogen or fluorine atom;

the carbon atom marked with an asterisk is an asymmetric carbon atom;

and their pharmaceutically acceptable salts.

Object of the present invention are the compounds of formula I in the form of stereoisomeric mixture as well as in the form of single stereoisomers.

The compounds of formula I object of the present invention are endowed with a mixed ACE-inhibitory and NEP-inhibitory activity and are useful in the treatment of cardiovascular diseases.

In the present description, unless otherwise specified, with the term biphenyl group we intend a 2-biphenyl, 3-biphenyl or 4-biphenyl group; with the term alkyl group we intend a straight or branched alkyl such as methyl, ethyl, n.propyl, isopropyl, n.butyl, sec-butyl, tert-butyl, isobutyl, n.pentyl, 2-pentyl, 3-pentyl, isopentyl, tert-pentyl, n.hexyl and iso-hexyl; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term aryl group we intend an aromatic group such as phenyl, 2-biphenyl, 3-biphenyl, 4-biphenyl, 1-naphthyl and 2-naphthyl or a 5 or 6 membered heterocyclic group containing 1 or 2 heteroatoms selected among nitrogen, oxygen and sulphur such as thiazole, isoxazole, oxazole, isothiazole, pyrazole, imidazole, thiophene, pyrrole, pyridine, pyrimidine and furan, optionally benzocondensed. Examples of pharmaceutically acceptable salts of the compounds of formula I are the salts with alkali or alkali-earth metals and the salts with pharmaceutically acceptable organic bases.

Preferred compounds of formula I are the compounds wherein R is a biphenyl group optionally substituted with from 1 to 3 substituents, the same or different, selected among chlorine or fluorine atoms or hydroxy groups; $R_1$ is a straight or branched $C_1$-$C_6$ alkyl group or an arylalkyl group having from 1 to 6 carbon atoms in the alkyl moiety wherein the aryl group is a phenyl or a biphenyl; $R_2$ is a straight or branched $C_1$-$C_6$ alkyl, an arylcarbonylaminoalkyl, an arylalkylcarbonylaminoalkyl or an arylalkyl group having from 1 to 6 carbon atoms in the alkyl moiety wherein the aryl group is a phenyl, m is 1 and X is hydrogen.

Still more preferred compounds of formula I are the Compounds wherein R is a 4-biphenyl group; $R_1$ is a straight or branched $C_3$-$C_6$ alkyl group; $R_2$ is an arylcarbonylaminoalkyl or an arylalkylcarbonylaminoalkyl group having from 1 to 3 carbon atoms in the alkyl moiety wherein the aryl group is a phenyl; m=1 and X=H.

Preferred examples of pharmaceutically acceptable salts of the compounds of formula I are the salts with alkali metals such as sodium, lithium and potassium.

The preparation of the compounds of formula I, object of the present invention, comprises the reaction between a compound of formula

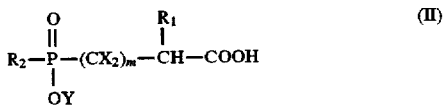

wherein $R_1$, $R_2$, m and X have the above reported meanings and Y represents a protective group, preferably a $C_1$-$C_4$ alkyl, a phenyl or a phenylalkyl group having from 1 to 4 carbon atoms in the alkyl moiety; and a biphenylalanine derivative of formula

wherein

R has the above reported meanings.

The condensation is carried out according to conventional techniques of the chemistry of peptides.

Before carrying out the reaction, it can be useful to properly protect the optional functional groups which could interfere in the reaction.

The optional protection is carried out according to conventional techniques.

For instance, it can be useful to protect the free carboxy function of the compound of formula III analogously to the OH function of the phosphinic group.

The evaluation of the usefulness of the optional protection as well as the selection of the kind of adopted protection, according to the reaction to be carried out and to the functional groups to be protected, are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc.

The compounds of formula II and III are known or easily prepared compounds according to known methods.

For instance, the compounds of formula II wherein m=1 and X=H can be prepared by reacting a phosphorylated derivative of formula

wherein $R_2$ and Y have the above reported meanings; with an acrylic acid derivative of formula

wherein $R_1$ has the above reported meanings and $R_3$ represents a hydrogen atom or, preferably, a protective group selected among a $C_1$-$C_4$ alkyl, a phenyl or a phenylalkyl having from 1 to 4 carbon atoms in the alkyl moiety.

The compounds of formula II wherein m=1 and X=F can be prepared by reacting a compound of formula

wherein $R_2$ and Y have the above reported meanings; with a α-halo-acid derivative of formula

wherein $R_1$ has the above reported meanings, Z is a chlorine or bromine atom and $R_3$ represents a hydrogen atom or, preferably, a protective group selected among a $C_1$-$C_4$ alkyl, a phenyl or a phenylalkyl group having from 1 to 4 carbon atoms in the alkyl moiety; in a basic medium.

The compounds of formula VI, in their turn, can be prepared from the corresponding phosphorylated derivatives of formula IV by treatment with sodium hydride and chlorodifluoromethane ($CHF_2Cl$).

The compounds of formula II wherein m=0 can be prepared as described in Tetrahedron Letters, 1984, 25, 4737–4740.

Alternatively, the compounds of formula I wherein m=1 and X=H, object of the present invention, can be prepared by reacting a phosphorylated derivative of formula IV with a compound of formula

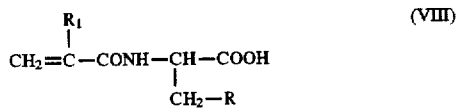

wherein

R and $R_1$ have the above reported meanings.

The compounds of formula VIII, in their turn, can be prepared by reacting an acrylic acid derivative of formula V wherein $R_3$ represents a hydrogen atom with a biphenylalanine derivative of formula III.

As previously pointed out, before carrying out said reactions it can be useful to properly protect the optional functional groups which could interfere in the reactions; the removal of the optional protective groups is carried out according to conventional techniques. The compounds of formula I in the form of single stereoisomers are prepared by stereoselective synthesis or by separation of the stereoisomeric mixture according to conventional techniques.

Also the preparation of the salts of the compounds of formula I, object of the invention, is carried out according to conventional techniques.

The compounds of formula I object of the present invention are endowed with a mixed ACE-inhibitory and NEP-inhibitory activity and are useful in the treatment of cardiovascular diseases.

The inhibitory activity of the compounds of formula I was evaluated by means of in vitro tests (example 24).

The inhibitory activity of the compounds of formula I, expressed as $IC_{50}$ value, is pharmacologically significant in that it results at nM concentrations.

For a practical use in therapy, the compounds of formula I can be formulated in solid or liquid pharmaceutical compositions, suitable to opal or parenteral administration.

The pharmaceutical compositions containing a therapeutically effective amount of a compound of formula I in admixture with a carrier for pharmaceutical use are, therefore, a further object of the present invention.

Specific examples of pharmaceutical compositions according to the present invention are tablets, coated tablets, capsules, granulates, solutions and suspensions suitable to opal administration, solutions and suspensions suitable to parenteral administration.

The pharmaceutical compositions object of the present invention are prepared according to conventional techniques.

For a practical use in therapy it can be useful to formulate the compounds of formula I in the form of pro-drugs, namely, of derivatives which enable the in vivo release of the pharmacologically active molecule that is to say of the corresponding compounds of formula I.

Specific examples of pro-drugs of the compounds of formula I are the esters of the carboxy group or of the phosphinic group.

The pro-drugs of the compounds of formula I, therefore, are within the scope of the present invention.

The daily dose of the compound of formula I or of the corresponding pro-drug will depend on different factors such as the seriousness of the disease, the individual response of the patient or the kind of formulation but it is usually comprised between 0.1 mg and 50 mg per Kg of body weight divided into a single dose or into more daily doses.

With the aim of better illustrating the present invention the following examples are now given.

EXAMPLE 1

Preparation of ethyl 2-ethoxycarbonyl-4-methylvalerate

Diethyl malonate (20 g; 124.8 mmoles) was added to a mixture of metallic sodium (2.87 g; 124.8 mmoles) dissolved in absolute ethanol (60 ml) at 50° C.

After 1 hour at room temperature isobutyl bromide 97% (16.78 g; 118.8 mmoles) was added dropwise.

After 2.5 hours at reflux temperature, the reaction mixture was kept at room temperature overnight.

After adding hydrochloric acid 1N up to pH 4–5, ethanol was evaporated and the residue was extracted with ethyl ether. After drying and evaporating the solvent at reduced pressure, the crude oil was purified by distillation at 78° C./2.5 mmHg after the removal of the exceeding diethyl malonate at 65° C./7 mmHg. Ethyl 2-ethoxycarbonyl-4-methylvalerate (14.4 g; 56% yield) was obtained as a colorless oil.

$^1$H-NMR (200 MHz, CDCl$_3$): δ (ppm): 0.87 (d, 6H); 1.21 (t, 6H); 1.52 (m, 1H); 1.75 (t, 2H); 3.47 (t, 1H); 4.15 (q, 4H).

EXAMPLE 2

Preparation of 2-ethoxycarbonyl-4-methylvaleric acid

A mixture of potassium hydroxide at 85% (3.6 g; 57.34 moles), water (10 ml) and ethanol (10 ml) was heated at 70° C. and hence ethyl 2-ethoxycarbonyl-4-methylvalerate (11.75 g; 54.34 mmoles), prepared as described in example 1, was therein added.

After keeping the reaction mixture at reflux temperature for 2 hours, ethanol was evaporated and the resultant solution was washed with ethyl acetate and acidified with concentrated hydrochloric acid.

After extracting with ethyl acetate, drying and evaporating the solvent at reduced pressure, 2-ethoxycarbonyl-4-methylvaleric acid (6.7 g; 65.5% yield) was obtained as a colorless oil.

$^1$H-NMR (200 MHz, CDCl$_3$): δ (ppm): 0.90 (d, 6H); 1.25 (t, 3H); 1.60 (m, 1H); 1.79 (t, 2H); 3.44 (t, 1H); 4.19 (g, 2H).

EXAMPLE 3

Preparation of ethyl 2-isobutylacrylate

A mixture of 2-ethoxycarbonyl-4-methylvaleric acid (6.7 g; 36 mmoles), prepared as described in example 2, piperidine (36 mmoles) and paraformaldehyde (1.08 g; 36 mmoles) in pyridine (6.48 ml) was heated under reflux for three hours.

After adding water (50 ml) and keeping under reflux for further two hours, the solution was diluted with water and extracted three times with ethyl ether.

The organic phase was washed twice with acidic water, dried and evaporated to dryness.

Ethyl 2-isobutylacrylate (3.2 g; 57% yield) was obtained as an oil.

$^1$H-NMR (200 MHz, CDCl$_3$): δ (ppm): 0.85 (d, 6H); 1.26 (t, 3H); 1.75 (m, 1H); 2.15 (d, 2H); 4.16 (q, 2H); 5.44 (d, 1H); 6.12 (d, 1H).

EXAMPLE 4

Preparation of methyl 4-phenylbutylphosphinic acid

A mixture of 4-phenylbutylphosphinic acid (10 g; 50.4 mmoles), prepared as described in Tetrahedron Letters, 27, 1751–1754, 1986, and trimethyl phosphite (83 ml; 706 moles) was heated at 60° C. for 8 hours.

By distilling the reaction mixture at reduced pressure (0.2 mmHg, b.p. 125°–127° C.), methyl 4-phenylbutylphosphinic acid (8.9 g; 83% yield) was obtained as a colorless oil.

$^1$H-NMR (200 MHz, CDCl$_3$): δ (ppm): 1.50–1.90 (m, 6H); 2.61 (t, 2H); 3.74 (d, 3H); 5.69, 8.32 (dt, 1H); 7.10–7.33 (m, 5H).

EXAMPLE 5

Preparation of benzyl [(4-phenylbutyl)(hydroxy)phosphinyl]acetate

Trimethylsilyl chloride (1.39 ml; 11 mmoles) and benzyl bromoacetate (0.86 ml) were added, at 0° C. and under nitrogen, to a solution of 4-phenylbutylphosphinic acid (1 g; 5 mmoles) and triethylamine (11 mmoles) in chloroform (20 ml).

The reaction mixture was kept under stirring for 16 hours at room temperature and was poured in water (10 ml) and concentrated hydrochloric acid (3.5 ml).

The mixture was extracted with methylene chloride and the organic phase was washed with brine and dried over sodium sulphate.

The solvent was evaporated at reduced pressure and the resultant oil was treated with a hexane: ethyl ether=1:1 mixture and filtered affording benzyl [(4-phenylbutyl)(hydroxy)phosphinyl]acetate (1.05 g; 61% yield) as a white solid.

$^1$H-NMR (200 MHz, CDCl$_3$): δ (ppm): 1.50–2.00 (m, 6H); 2.55 (bt, 2H); 2.95 (d, 2H); 5.12 (s, 2H); 7.06–7.38 (m, 10H).

EXAMPLE 6
Preparation of [(4-phenylbutyl)(methoxy)phosphinyl]acetic acid

A solution of benzyl [(4-phenylbutyl)(hydroxy)phosphinyl]acetate (1.05 g; 3 moles), prepared as described in example 5, in methylene chloride (10 ml) was treated with a slight excess of an etheral solution of diazomethane up to the formation of a persistent yellow solution.

The solution was treated with acetic acid up to decoloration and the solvent was evaporated under vacuum.

The resultant etude oil (1.16 g) was dissolved in methanol (100 ml) and hydrogenated into a Parr apparatus in the presence of palladium on charcoal at 10% (0.3 g).

By filtering off the catalyst and evaporating the reaction mixture under vacuum, [(4-phenylbutyl)(methoxy)phosphinyl]acetic acid (0.725 g; 87% yield) was obtained as a colorless oil.

$^1$H-NMR (200 MHz, CDCl$_3$): δ (ppm): 1.50–2.10 (m, 6H); 2.60 (bt, 2H); 2.92 (d, 2H); 3.74 (d, 3H); 7.08–7.31 (m, 5H).

EXAMPLE 7
Preparation of methyl 3-[(3-phenylpropyl)(methoxy)phosphinyl]-2-isobutyl-propionate A solution of sodium (0.345 g; 15 mmoles) in methanol (4 ml) was added dropwise in three hours, at 0° C. and under nitrogen, to a solution of methyl 3-phenylpropylphosphinic acid (2.97 g; 15 mmoles), prepared as described in J. Med. Chem. 1989, 32, 1652–1661, and ethyl 2-isobutylacrylate (2.65 g; 17 mmoles), prepared as described in example 3.

After one night at room temperature, the reaction mixture was diluted with water, acidified with diluted hydrochloric acid up to neutral pH and extracted twice with ethyl acetate.

The organic phase was washed twice with an aqueous solution of potassium bicarbonate, dried and evaporated to dryness.

The crude residue (2.7 g) was purified by silica gel column chromatography (eluent CH$_2$Cl$_2$:CH$_3$OH=95:5) affording methyl 3-[(3-phenylpropyl)(methoxy)phosphinyl]-2-isobutyl-propionate (2 g; 40.6% yield).

$^1$H-NMR (300 MHz, CDCl$_3$): δ (ppm): 0.87 (d, 3H); 0.90 (d, 3H); 1.30 (m, 1H); 1.42–1.95 (m, 6H); 2.14 (m, 1H); 2.68 (t, 2H); 2.77 (m, 1H); 3.60–3.71 (2d, 3H); 3.65 (s, 3H); 7.10–7.35 (m, 5H).

By working in a similar way and by using methyl 4-phenylbutylphosphinic acid as starting material, prepared as described in example 4, the following compound was prepared:

methyl 3-[(4-phenylbutyl)(methoxy)phosphinyl]-2-isobutyl-propionate $^1$H-NMR (200 MHz, CDCl$_3$): δ (ppm): 0.88 (dd, 6H); 1.15–1.81 (m, 10H); 2.00–2.25 (m, 1H); 2.61 (t, 2H); 2.75 (m, 1H); 3.63 (dd, 3H); 3.67 (s, 3H); 7.07–7.31 (m, 5H).

EXAMPLE 8
Preparation of 3-[(3-phenylpropyl)(methoxy)phosphinyl]-2-isobutyl-propionic acid A solution of methyl 3-[(3-phenylpropyl)(methoxy)phosphinyl]-2-isobutyl-propionate (0.778 g; 2.29 mmoles), prepared as described in example 7, and sodium hydroxide 1N (2.29 ml; 2.29 mmoles) in methanol (15 ml), under nitrogen, was kept at 60° C. for 2 days.

After diluting with water and washing with ethyl acetate, the aqueous phase was acidified and extracted with ethyl acetate.

The organic phase, after drying and evaporating the solvent to dryness, furnished 3-[(3-phenylpropyl)(methoxy)phosphinyl]-2-isobutyl-propionic acid (0.6 g; 80.4% yield).

$^1$H-NMR (200 MHz, CDCl$_3$): δ (ppm): 0.89 (2d, 6H); 1.28 (m, 1H); 1.50–1.20 (m, 7H); 2.20 (m, 1H); 2.67 (t, 1H); 2.75 (m, 1H); 3.68 (2d, 3H); 7.10–7.35 (m, 5H).

By working in a similar way the following compound was prepared:

3-[(4-phenylbutyl)(methoxy)phosphinyl]-2-isobutyl-propionic acid $^1$H-NMR (200 MHz, CDCl$_3$): δ (ppm): 0.90 (m, 6H); 1.10–1.90 (m, 10H); 2.05–2.35 (m, 1H); 2.60 (t, 2H); 2.78 (m, 1H); 3.68 (d, 3H); 7.10–7.32 (m, 5H).

EXAMPLE 9
Preparation of (1,1'-biphenyl-4-yl)-L-alanine methyl ester hydrochloride Thionyl chloride (0.043 ml; 0.586 mmoles) was added at room temperature to a solution of N-tert-butoxycarbonyl-(1,1'-biphenyl-4-yl)-L-alanine (100 mg; 0.293 mmoles) in methanol (2 ml).

After 24 hours, the reaction mixture was concentrated at small volume by evaporation under vacuum affording (1,1'-biphenyl-4-yl)-L-alanine methyl ester hydrochloride with a practically quantitative yield (85 mg) as a crystalline solid.

m.p. 215°–216° C.

$^1$H-NMR (200 MHz, DMSO-d$_6$): δ (ppm): 3.15 (dd, 2H); 3.70 (s, 3H); 4.30 (t, 1H); 7.25–7.52 (m, 5H); 7.65 (m, 4H).

EXAMPLE 10
Preparation of N-[3-[(3-phenylpropyl)(methoxy)phosphinyl]-2-isobutyl-propionyl]-(1,1'-biphenyl-4-yl)-L-alanine methyl ester A solution of dicyclohexylcarbodiimide (0.433 g; 2.1 mmoles) in dioxane (15 ml) was added, at 0° C. and under stirring, to a solution of 3-[(3-phenylpropyl)(methoxy)phosphinyl]-2-isobutyl-propionic acid (0.62 g; 2.1 mmoles), prepared as described in example 8, and N-hydroxysuccinimide (0.242 g; 2.1 mmoles) in dioxane (15 ml).

After two hours at room temperature, dicyclohexylurea was filtered off and (1,1'-biphenyl-4-yl)-L-alanine methyl ester hydrochloride (0.56 g; 1.91 mmoles), prepared as described in example 9, and triethylamine (0.266 ml; 1.91 mmoles) were added to the resultant solution.

After keeping fop one night at room temperature and heating at 60° C. for 4 hours, the reaction mixture was diluted with water and extracted with ethyl acetate.

After drying on sodium sulphate, the resultant crude from the evaporation of the solvent was silica gel column chromatographed (eluent CH$_2$Cl$_2$:CH$_3$OH=95:5) affording N-[3-[(3-phenylpropyl)(methoxy)phosphinyl]-2-isobutyl-propionyl]-(1,1'-biphenyl-4-yl)-L-alanine methyl ester (0.24 g; 22.3% yield), which was used as such in the subsequent reaction without further purifications.

$^1$H-NMR (200 MHz, CDCl$_3$): δ (ppm): 0.76 (d, 6H); 1.00–1.40 (m, 3H); 1.47–1.74 (m, 3H); 1.75–1.98 (m, 2H); 2.00–2.28 (m, 1H); 2.53 (m, 1H); 2.64 (t, 2H); 3.03 (dd, 1H); 3.18 (dd, 1H); 3.57 (d, 3H); 3.72 (s, 3H); 4.87 (q, 1H); 7.10–7.60 (m, 14H).

By working in a similar way the following compounds were prepared:

N-[3-[(4-phenylbutyl)(methoxy)phosphinyl]-2-isobutyl-propionyl]-(1,1'-biphenyl-4-yl)-L-alanine methyl ester $^1$H-NMR (200 MHz, CDCl$_3$): δ (ppm): 0.70–0.90 (m, 6H); 1.00–1.80 (m, 10H); 1.85–2.20 (m, 1H); 2.50–2.70 (m, 3H); 3.00–3.25 (m, 2H); 3.46–3.65 (m, 3H); 3.68 (m, 3H); 4.87 (m, 1H); 7.00–7.60 (m, 14H).

N-[[(4-phenylbutyl)(methoxy)phosphinyl]acetyl]-(1,1'-biphenyl-4-yl)-L-alanine methyl ester $^1$H-NMR (200 MHz, CDCl$_3$): δ (ppm): 1.50–1.90 (m, 6H); 2.55 (m, 2H); 2.77 (m, 2H); 3.04 (dd, 1H); 3.22 (m, 1H); 3.54, 3.67 (dd, 3H); 3.72 (s, 3H); 4.84 (m, 1H); 7.00–7.60 (m, 14H).

By working in a similar way and by using 3-[(benzyloxycarbonylaminomethyl) (methoxy)phosphinyl]-2-isobutyl-propionic acid as starting material, prepared as described in J. Am. Chem. Soc. 1991, 113, 297–307, the following compound was prepared:

N-[3-[(benzyloxycarbonylaminomethyl)(methoxy)phosphinyl]-2-isobutyl-propionyl]-(1,1'-biphenyl-4-yl)-L-alanine methyl ester $^1$H-NMR (200 MHz, CDCl$_3$): δ (ppm): 0.80–0.90 (m, 6H); 1.00–2.30 (m, 5H); 2.50–2.80 (m, 1H); 3.12 (bd, 2H); 3.30–3.80 (m, 8H); 4.86 (m, 1H); 5.07 (dd, 3H); 7.18–7.58 (m, 14H).

EXAMPLE 11

Preparation of N-(2-isobutyl-acryloyl)-(1,1'-biphenyl-4-yl)-L-alanine methyl ester A suspension of (1,1'-biphenyl-4-yl)-L-alanine methyl ester hydrochloride (7.03 g; 24 mmoles), prepared as described in example 9, 2-isobutyl-acrylic acid (3.7 g; 28.9 mmoles), triethylamine (4.01 ml; 28.9 mmoles) and dicyclohexylcarbodiimide (5.95 g; 28.9 mmoles) in methylene chloride (140 ml) was kept under stirring at room temperature for 21 hours.

The resultant precipitate was filtered off and the organic phase was washed with water, dried on sodium sulphate and evaporated at reduced pressure.

The resultant crude was purified by silica gel column chromatography (eluent 40°–60° C. petroleum ether: ethyl acetate=80:20) affording N-(2-isobutyl-acryloyl)-(1,1'-biphenyl-4-yl)-L-alanine methyl ester (4.17 g; 47% yield) as a white solid.

$^1$H-NMR (200 MHz, CDCl$_3$): δ (ppm): 0.93 (d, 6H); 1.50–1.75 (m, 1H); 2.15 (d, 2H); 3.08–3.30 (m, 2H); 3.75 (s, 3H); 4.95 (m, 1H); 5.21 (s, 1H); 5.58 (s, 1H); 7.00–7.60 (m, 9H).

By working in a similar way the following compound was prepared:

N-(2-isopropyl-acryloyl)-(1,1'-biphenyl-4-yl)-L-alanine methyl ester $^1$H-NMR (200 MHz, CDCl$_3$): δ (ppm): 1.00 (m, 6H); 2.68–2.85 (m, 1H); 3.05–3.31 (m, 2H); 3.75 (s, 3H); 4.90–5.02 (m, 1H); 5.20 (s, 1H); 5.41 (s, 1H); 6.18 (d, 1H); 7.15–7.65 (m, 9H).

EXAMPLE 12

Preparation of 1,3,5-tris[2-phenylethyl]-hexahydrotriazine

2-Phenylethylamine (57.7 ml) was added to an aqueous solution of formaldehyde at 40% (34.3 ml; 0.457 moles), keeping the temperature below 20° C.

The reaction mixture was kept under stirring at room temperature for 24 hours.

After that, methylene chloride was therein added and the reaction mixture was washed with water.

The phases were separated and the organic phase was dried on sodium sulphate and evaporated at reduced pressure obtaining 1,3,5-tris[2-phenylethyl]-hexahydrotriazine (57 g; 94% yield) as an oil which was used as such in the subsequent reaction without further purifications.

EXAMPLE 13

Preparation N-[[(diethoxy-methyl)(ethoxy)phosphinyl]methyl]-2-phenylethylamine

A mixture of 1,3,5-tris[2-phenylethyl]-hexahydrotriazine (3.4 g; 8.5 mmoles), prepared as described in example 12, and ethyl (diethoxy-methyl)phosphinic acid (3.4 g; 25.5 mmoles), prepared as described in Aust. J. Chem., 1980, 33, 287–94, in toluene (50 ml) was heated at reflux for 2 hours.

The reaction mixture was evaporated under vacuum obtaining N-[[(diethoxy-methyl)(ethoxy)phosphinyl]methyl]-2-phenylethylamine (8.4 g) as a colorless oil which was used as such in the subsequent reaction without further purifications.

EXAMPLE 14

Preparation of (2-phenylethylaminomethyl)phosphinic acid

A mixture of N-[[(diethoxy-methyl)(ethoxy)phosphinyl]methyl]-2-phenylethylamine (24.9 mmoles), prepared as described in example 13, in concentrated hydrochloric acid (40 ml) was heated at reflux for 2 hours.

The reaction mixture was evaporated at reduced pressure and the residue was collected with ethyl acetate and filtered.

The thus obtained solid was dissolved in warm methanol (50 ml) and filtered.

The resultant solution was then treated with an excess of propylene oxide and after 45 minutes a precipitate was formed.

The precipitate was filtered and dried under vacuum at 40° C. affording (2-phenylethylaminomethyl)phosphinic acid (2.07 g; 42% yield) as a white solid which was used as such in the subsequent reaction without further purifications.

$^1$H-NMR (200 MHz, D$_2$O): δ (ppm): 2.85 (t, 2H); 2.95 (dd, 2H); 3.25 (t, 2H); 5.60 (t, 0.5H); 7.10–7.30 (m, 5H); 8.33 (t, 0.5H).

EXAMPLE 15

Preparation of (N-benzyloxycarbonyl-2-phenylethylaminomethyl)phosphinic acid

Benzylchloroformate (1.94 ml; 12.35 mmoles) and an aqueous solution of sodium hydroxide 1N (12.35 ml; 12.35 mmoles) were simultaneously added, below 5° C. and under nitrogen atmosphere, to a solution of (2-phenylethylaminomethyl)phosphinic acid (2.05 g; 10.29 mmoles), prepared as described in example 14, in an aqueous solution of sodium hydroxide 1N (10.29 ml; 10.29 mmoles).

The reaction mixture was kept under stirring at room temperature for one hour.

After that, water (20 ml) was therein added and the mixture was washed with ethyl acetate and acidified with hydrochloric acid. The reaction mixture was extracted with ethyl acetate and the organic phase was washed with water and dried on sodium sulphate. By evaporating the solvent at reduced pressure, (N-benzyloxycarbonyl-2-phenylethylaminomethyl)phosphinic acid (3.3 g; 46% yield) was obtained as a viscous oil which was used as such in the subsequent reaction without further purifications.

$^1$H-NMR (200 MHz, CDCl$_3$): δ (ppm): 2.80 (m, 2H); 3.33 (t, 2H); 3.57 (m, 2H); 5.10 (d, 2H); 5.61 (d, 0.5H); 7.00–7.40 (m, 10H); 8.50 (d, 0.5H).

EXAMPLE 16

Preparation of methyl (N-benzyloxycarbonyl-2-phenylethylaminomethyl)phosphinic acid A slight excess of an etheral solution of diazomethane was added at 0° C. to a solution of (N-benzyloxycarbonyl-2-phenylethylaminomethyl)-phosphinic acid (3.3 g; 9.9 mmoles), prepared as described in example 15, in methylene chloride (30 ml) up to the formation of a persistent yellow solution.

Acetic acid was therein added up to decoloration of the reaction mixture which was then washed with water.

The collected organic phase was dried on sodium sulphate and evaporated at reduced pressure affording methyl (N-benzyloxycarbonyl-2-phenylethylaminomethyl) phosphinic acid (3.25 g; 94% yield) as a clear oil.

$^1$H-NMR (200 MHz, CDCl$_3$): δ (ppm): 2.82 (m, 2H); 3.30–3.80 (m, 7H); 5.12 (d, 2H); 5.65 (d, 0.5H); 7.00–7.40 (m, 10H); 8.46 (d, 0.5H).

EXAMPLE 17
Preparation of N-[3-[(N'-benzyloxycarbonyl-2-phenylethylaminomethyl)(methoxy)phosphinyl]-2-isobutyl-propionyl]-(1,1'-biphenyl-4-yl)-L-alanine methyl ester A solution of sodium hydroxide at 55% (0.395 g; 9.07 mmoles) was added to a solution of methyl (N-benzyloxycarbonyl-2-phenylethyl-aminomethyl) phosphinic acid (3.15 g; 9.07 mmoles), prepared as described in example 16, and N-(2-isobutyl-acryloyl)-(1,1'-biphenyl-4-yl)-L-alanine methyl ester (3.31 g; 9.07 mmoles), prepared as described in example 11, in dimethylformamide (50 ml) at 5° C. The reaction mixture was kept under stirring at room temperature for 6 hours and then was poured in water containing concentrated hydrochloric acid (2 ml).

By extracting with ethyl acetate, washing the organic phase with water, drying on sodium sulphate and evaporating at reduced pressure, a crude oil was obtained which was purified by silica gel column chromatography (eluent ethyl acetate) affording N-[3-[(N'-benzyloxycarbonyl-2-phenylethylaminomethyl)(methoxy)phosphinyl]-2-isobutyl-propionyl]-(1,1'-biphenyl-4-yl)-L-alanine methyl ester (1.66 g; 26% yield) as a colorless oil.

$^1$H-NMR (200 MHz, CDCl$_3$+D$_2$O): δ (ppm): 0.72 (d, 6H); 1.00–1.35 (m, 2H); 1.45–1.90 (m, 2H); 1.95–2.20 (m, 1H); 2.40–3.80 (m, 15H); 4.80–5.15 (m, 3H); 7.00–7.60 (m, 19H).

By working in a similar way the following compound was prepared:

N-[3-[(4-phenylbutyl)(methoxy)phosphinyl]-2-isopropyl-propionyl]-(1,1'-biphenyl-4-yl)-L-alanine methyl ester $^1$H-NMR (200 MHz, CDCl$_3$): δ (ppm): 0.70–0.90 (m, 6H); 1.50–2.40 (m, 9H); 2.50–2.65 (m, 3H); 3.00–3.25 (m, 2H); 3.50–3.70 (m, 6H); 4.80–5.00 (m, 1H); 6.45–6.55 (m, 1H); 7.03–7.60 (m, 14H).

EXAMPLE 18
Preparation of N-[3-[(3-phenylpropyl)(hydroxy)phosphinyl]-2-isobutyl-propionyl]-(1,1'-biphenyl-4-yl)-L-alanine dilithium salt (Compound 1)

A solution of N-[3-[(3-phenylpropyl)(methoxy) phosphinyl]-2-isobutyl-propionyl]-(1,1'-biphenyl-4-yl)-L-alanine methyl ester (0.24 g; 0.43 mmoles), prepared as described in example 10, and lithium hydroxide monohydrate (54 mg; 1.27 mmoles) in a water:tetrahydrofuran=1:2 mixture was kept at room temperature for 72 hours.

After evaporation of the solvent under vacuum to small volume, the residue was collected with water (5 ml) and the aqueous solution was washed with ethyl acetate (2×10 ml).

The aqueous phase was acidified with hydrochloric acid 1N.

After extracting with ethyl acetate and drying on sodium sulphate, the solvent was evaporated.

The crude was silica Eel column chromatographed (eluent CH$_2$Cl$_2$:CH$_3$OH:CH$_3$COOH=90:10:1) affording N-[3-[(3-phenylpropyl)(hydroxy)phosphinyl]-2-isobutyl-propionyl]-(1,1'-biphenyl-4-yl-L-alanine dilithium salt (70 mg; 31% yield) as an oil which tends to solidify.

$^1$H-NMR (200 MHz, CDCl$_3$): δ (ppm): 0.63 (t, 3H); 0.77 (t, 3H); 0.80–2.20 (m, 11H); 2.57 (g, 2H); 2.71 (m, 1H); 2.86–3.45 (m, 2H); 4.76 (m, 0.5H); 4.98 (m, 0.5H); 7.00–7.60 (m, 14H).

By working in a similar way the following compounds were prepared:

N-[3-[(4-phenylbutyl)(hydroxy)phosphinyl]-2-isobutyl-propionyl]-(1,1'-biphenyl-4-yl)-L-alanine disodium salt (Compound 2)

$^1$H-NMR (200 MHz, D$_2$O): δ (ppm): 0.29–0.69 (m, 6H); 0.78–1.63 (m, 11H); 2.17–2.51 (m, 3H); 2.63–3.19 (m, 2H); 4.30–4.48 (m, 1H); 6.90–7.45 (m, 14H).

N-[[(4-phenylbutyl)(hydroxy)phosphinyl]-acetyl]-(1,1'-biphenyl-4-yl)-L-alanine disodium salt (Compound 3)

$^1$H-NMR (200 MHz, D$_2$O): δ (ppm): 0.91–1.25 (m, 6H); 2.20 (m, 2H); 2.24–2.58 (m, 2H); 2.77 (dd, 1H); 3.13 (dd, 1H); 4.33 (dd, 1H); 6.80–7.50 (m, 14H).

N-[3-[(4-phenylbutyl)(hydroxy)phosphinyl]-2-isopropyl-propionyl]-(1,1'-biphenyl-4-yl)-L-alanine disodium salt (Compound 4)

$^1$H-NMR (200 MHz, D$_2$O): δ (ppm): 0.38–0.76 (m, 6H); 0.82–2.22 (m, 9H); 2.35–2.42 (m, 2H); 2.34–2.49 (m, 1H); 2.69–3.16 (m, 2H); 4.19–4.26, 4.40–4.47 (2m, 1H); 6.89–7.51 (m, 14H).

EXAMPLE 19
Preparation of N-[3-[(N'-benzyloxycarbonyl-2-phenylethylaminomethyl)(hydroxy)phosphinyl]-2-isobutyl-propionyl]-(1,1'-biphenyl-4-yl)-L-alanine A solution of N-[3-[(N'-benzyloxycarbonyl-2-phenylethylaminomethyl)-(methoxy)phosphinyl]-2-isobutyl-propionyl]-(1,1'-biphenyl-4-yl)-L-alanine methyl ester (1.64 g; 2.3 mmoles), prepared as described in example 17, and lithium hydroxide monohydrate (0.386 g; 9.2 mmoles) in a water:tetrahydrofuran=1:1 mixture (60 ml) was kept under stirring at room temperature for 24 hours and under nitrogen atmosphere. The reaction mixture was diluted with water and treated with concentrated hydrochloric acid (1 ml).

The mixture was then extracted with ethyl acetate and the organic phase was dried on sodium sulphate and evaporated under vacuum affording N-[3-[(N'-benzyloxycarbonyl-2-phenylethylaminomethyl)(hydroxy)phosphinyl]-2-isobutyl-propionyl]-(1,1'-biphenyl-4-yl)-L-alanine (1.55 g; 98% yield).

$^1$H-NMR (200 MHz, DMSO-d$_6$): δ (ppm): 0.60 (d, 3H); 0.68 (d, 3H); 0.90–1.95 (m, 5H); 2.64 (m, 1H); 2.83 (t, 2H); 2.90 (dd, 1H); 3.20 (dd, 1H); 3.45–3.65 (m, 4H); 4.60 (m, 1H); 5.05 (s, 2H); 7.10–7.65 (m, 19H).

EXAMPLE 20
Preparation of N-[3-[(2-phenylethylaminomethyl)(hydroxy) phosphinyl]-2-isobutyl-propionyl]-(1,1'-biphenyl-4-yl)-L-alanine (Compound 5)

A solution of N-[3-[(N'-benzyloxycarbonyl-2-phenylethylaminomethyl)-(hydroxy)phosphinyl]-2-isobutyl-propionyl]-(1,1'-biphenyl-4-yl)-L-alanine (1.53 g; 2.23 mmoles), prepared as described in example 19, in ethanol at 80% (100 ml) was hydrogenated into a Parr apparatus in the presence of palladium on charcoal at 10% (0.3 g).

When the hydrogen absorption was over, the catalyst was filtered off and by evaporating the resultant solution under vacuum a crystalline product was formed.

After filtration and drying under vacuum at 40° C. N-[3-[(2-phenylethylaminomethyl)(hydroxy)phosphinyl]-2-isobutyl-propionyl]-(1,1'-biphenyl-4-yl)-L-alanine (0.9 g; 73% yield) was thus obtained as a white solid.

m.p. 229°–230° C.

$^1$H-NMR (200 MHz, DMSO-d$_6$): δ (ppm): 0.63 (d, 3H); 0.72 (d, 3H); 1.05 (m, 2H); 1.30–1.85 (m, 3H); 2.60 (m, 1H); 2.80–3.32 (m, 8H); 4.62 (m, 1H); 7.20–7.61 (m, 14H).

EXAMPLE 21

Preparation of N-[3-[(aminomethyl)(methoxy)phosphinyl]-2-isobutylpropionyl]-(1,1'-biphenyl-4-yl)-L-alanine methyl ester hydrochloride A solution of N-[3-[(benzyloxycarbonylaminomethyl)(methoxy)phosphinyl]-2-isobutyl-propionyl]-(1,1'-biphenyl-4-yl)-L-alanine methyl ester (1.75 g; 2.87 mmoles), prepared as described in example 10, and hydrochloride acid 12N (0.24 ml; 2.87 mmoles) in methanol (50 ml) was hydrogenated into a Parr apparatus at room temperature in the presence of catalytic amounts of palladium on charcoal.

The catalyst was then filtered off and the solvent was evaporated at reduced pressure affording N-[3-[(aminomethyl)(methoxy)phosphinyl]-2-isobutyl-propionyl]-(1,1'-biphenyl-4-yl)-L-alanine methyl ester hydrochloride (1.43 g; 97% yield).

$^1$H-NMR (200 MHz, D$_2$O): δ (ppm): 0.56–0.70 (2d, 6H); 1.00–1.40 (m, 3H); 1.80–2.03 (m, 2H); 2.45–2.70 (m, 1H); 2.80–3.20 (m, 4H); 3.35–3.52 (2d, 3H); 3.55 (s, 3H); 4.55 (m, 1H); 7.12–7.50 (m, 9H).

EXAMPLE 22

Preparation of N-[3-[(benzoylaminomethyl)(methoxy)phosphinyl]-2-isobutyl-propionyl]-(1,1'-biphenyl-4-yl)-L-alanine methyl ester Benzoyl chloride (0.191 ml; 1.64 mmoles) and triethylamine (0.457 ml; 3.29 mmoles) were added at room temperature and under stirring to a solution of N-[3-[(aminomethyl)(methoxy)phosphinyl]-2-isobutyl-propionyl]-(1,1'-biphenyl-4-yl)-L-alanine methyl ester hydrochloride (0.7 g; 1.37 mmoles), prepared as described in example 21, in methylene chloride (20 ml).

After 30 minutes the reaction mixture was washed with an aqueous solution of potassium bisulphite at 2% (10 ml), water, an aqueous solution of sodium bicarbonate at 2% (10 ml) and water, respectively.

The collected organic phase was dried on sodium sulphate and evaporated at reduced pressure.

The residue was purified by silica gel column chromatography (eluent methylene chloride:methanol=97:3) affording N-[3-[(benzoylaminomethyl)(methoxy)phosphinyl]-2-isobutyl-propionyl]-(1,1'-biphenyl-4-yl)-L-alanine methyl ester (0.66 g; 83% yield).

$^1$H-NMR (200 MHz, CDCl$_3$): δ (ppm): 0.78–0.94 (2d, 6H); 1.20–2.35 (m, 5H); 2.60–2.90 (m, 1H); 2.95–3.26 (m, 2H); 3.60–4.30 (m, 8H); 4.75–5.00 (m, 1H); 7.12–7.55 (m, 12H); 7.83 (d, 2H).

EXAMPLE 23

Preparation of N-[3-[(benzoylaminomethyl)(hydroxy)phosphinyl]-2-isobutyl-propionyl]-(1,1'-biphenyl-4-yl)-L-alanine (Compound 6)

By working as described in example 19 and by using N-[3-[(benzoylaminomethyl)(methoxy)phosphinyl]-2-isobutyl-propionyl]-(1,1'-biphenyl-4-yl)-L-alanine methyl ester (0.64 g; 1.11 mmoles), prepared as described in example 22, N-[3-[(benzoylaminomethyl)(hydroxy)phosphinyl]-2-isobutyl-propionyl]-(1,1'-biphenyl-4-yl)-L-alanine (0.56 g; 92% yield) was obtained as a white crystalline solid.

m.p. 148°–150° C.

$^1$H-NMR (200 MHz, D$_2$O+NaHCO$_3$): δ (ppm): 0.60 (d, 3H); 0.66 (d, 3H); 1.08–1.60 (m, 5H) 2.41–2.60 (m, 1H); 2.60–3.25 (m, 4H); 4.35–4.42 (m, 1H); 7.08–7.50 (m, 14H).

By working in a similar way the following compound was prepared:

N-[3-[(phenylacetylaminomethyl)(hydroxy)phosphinyl]-2-isobutyl-propionyl]-(1,1'-biphenyl-4-yl)-L-alanine (Compound 7)

m.p. 176°–177° C.

$^1$H-NMR (200 MHz, D$_2$O+NaHCO$_3$): δ (ppm): 0.59, 0.65 (2d, 6H); 1.08–1.45 (m, 5H); 2.32–2.47 (m, 1H); 2.50–3.11 (m, 4H); 3.26 (s, 2H); 4.32–4.39 (m, 1H); 7.04–7.46 (m, 14H).

EXAMPLE 24

"In vitro" evaluation of the pharmacologic activity a) NEP-inhibitory activity

The NEP-inhibitory activity was evaluated according to the method reported in the literature by C. Llorens et al., in Eur. J. Pharmacol., 69, (1981), 113–116.

Membranes from kidney cortex were prepared according to the following procedure.

By working at 0°–4° C., kidneys were removed from male Sprague-Dawley rats weighing approximately 300 g.

Cortex was carefully dissected, finely minced and suspended in a homogenization buffer (10 mM sodium phosphate pH 7.4 containing 1 mM MgCl$_2$, 30 mM NaCl, 0.02% NAN$_3$) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use. The NEP-inhibitory activity was evaluated by using the following method.

Aliquots of the membrane suspension prepared as above described (concentration 5 μg/ml of proteins) were preincubated in the presence of an aminopeptidase inhibitor (Bestatin—1 mM) for 10 minutes at 30° C.

[$^3$H][Leu$^5$]-enkephaline (15 nM) and buffer TRIS/HCl pH 7.4 (50 mM) were added in order to obtain a final volume of 100 μl. Incubation (20 minutes at 30° C.) was stopped by adding HCl 0.1M (100 μl).

The formation of the metabolite [$^3$H]Tyr-Gly-Gly was quantified by chromatography on polystyrene columns (Porapak Q). The percentage of inhibition of the metabolite formation in the membrane preparations treated with the compounds of formula I, in comparison to the untreated membrane preparations, was expressed as IC$_{50}$ value (nM).

b) ACE-inhibitory activity

The ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) with 50 μl of the compound of formula I were preincubated in thermostated cuvettes at 37° C.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 nm was recorded in continuo for 5 minutes.

The percentage of the enzyme inhibition in the preparations treated with the compounds of formula I with respect to the untreated preparations was expressed as IC$_{50}$ value (nM).

The compounds of formula I were tested in the form of lithium or sodium salts.

We report in the following table 1 the $IC_{50}$ values (nM) related to the ACE-inhibitory activity and NEP-inhibitory activity of compounds 1, 2, 6 and 7.

TABLE 1

ACE-inhibitory and NEP-inhibitory activity of compound 1, compound 2, compound 6 and compound 7 expressed as $IC_{50}$ (nM).

| Compound | ACE-inhibitory activity $IC_{50}$ (nM) | NEP-inhibitory activity $IC_{50}$ (nM) |
|---|---|---|
| 1 | 70 | 368 |
| 2 | 24 | 220 |
| 6 | 4.6 | 7.7 |
| 7 | 183.0 | 30.1 |

The data reported in table 1 show that the compounds of formula I, object of the present invention, are endowed with a significant mixed ACE/NEP inhibitory activity.

We claim:

1. A compound of formula

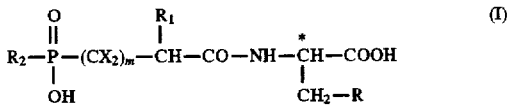

wherein

R is a biphenyl group optionally substituted by one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_1$ is a hydrogen atom, a straight or branched $C_1$–$C_6$ alkyl group or an arylalkyl group having from 1 to 6 carbon atoms in the alkyl moiety wherein the aryl is a phenyl, a biphenyl, a naphthyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

$R_2$ is a straight or branched $C_1$–$C_6$ alkyl group, optionally containing one or more fluorine atoms or one or more —NH— groups, an arylalkyl, an arylcarbonylaminoalkyl, an arylalkylcarbonylaminoalkyl or an arylaminocarbonylalkyl group having from 1 to 6 carbon atoms and optionally one or more —NH— groups in the alkyl moiety, the aryl being optionally substituted by one or more substituents, the same or different, selected among halogen atoms, hydroxy groups, alkoxy, alkyl, thioalkyl or alkoxycarbonyl groups having from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino groups having from 1 to 6 carbon atoms in the alkyl moiety, mono- or di-alkylaminocarbonyl groups having from 1 to 6 carbon atoms in the alkyl moiety;

m is 0 or 1;

X is a hydrogen or fluorine atom;

the carbon atom marked with an asterisk is an asymmetric carbon atom;

and pharmaceutically acceptable salts thereof.

2. A compound according to claim 1 wherein R is a biphenyl group optionally substituted with from 1 to 3 substituents, the same or different, selected among chlorine or fluorine atoms or hydroxy groups; $R_1$ is a straight or branched $C_1$–$C_6$ alkyl group or an arylalkyl group having from 1 to 6 carbon atoms in the alkyl moiety wherein the aryl group is a phenyl or a bipheny; $R_2$ is a straight or branched $C_1$–$C_6$ alkyl, an arylcarbonylaminoalkyl, an arylalkylcarbonylaminoalkyl or an arylalkyl group having from 1 to 6 carbon atoms in the alkyl moiety wherein the aryl group is a phenyl, m is 1 and X is hydrogen.

3. A compound according to claim 2 wherein R is a 4-biphenyl group; $R_1$ is a straight or branched $C_3$–$C_6$ alkyl group; $R_2$ is an arylcarbonylaminoalkyl or an arylalkylcarbonylaminoalkyl group having from 1 to 3 carbon atoms in the alkyl moiety wherein the aryl group is a phenyl, m=1 and X=H.

4. A compound according to claim 1 in the form of a salt with an alkali metal selected among sodium, lithium and potassium.

5. A process for the preparation of a compound of formula I according to claim 1 which comprises the reaction between a compound of formula

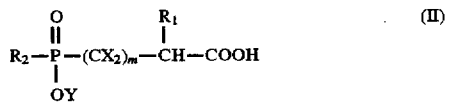

wherein $R_1$, $R_2$, m and X have the meanings reported in claim 1 and Y represents a protective group selected among a $C_1$–$C_4$ alkyl, a phenyl or a phenylalkyl group having from 1 to 4 carbon atoms in the alkyl moiety;

and a biphenylalanine derivative of formula

wherein

R has the meanings reported in claim 1.

6. A process for the preparation of a compound of formula I wherein m=1 and X=H according to claim I which comprises the reaction between a compound of formula

wherein $R_2$ has the meanings reported in claim 1 and Y represents a protective group selected among a $C_1$–$C_4$ alkyl, a phenyl or a phenylalkyl group having from 1 to 4 carbon atoms in the alkyl moiety; and a compound of formula

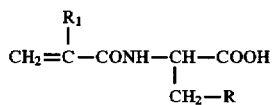

(VIII)

wherein

R and $R_1$ have the meanings reported in claim 1.

7. A pharmaceutical composition containing a therapeutically effective amount of a compound of formula I according to claim 1 in admixture with a carrier for pharmaceutical use.

8. A pharmaceutical composition according to claim 7 for the treatment of cardiovascular diseases.

* * * * *